(12) United States Patent
Blin et al.

(10) Patent No.: US 8,124,112 B2
(45) Date of Patent: Feb. 28, 2012

(54) COSMETIC COMPOSITION COMPRISING AT LEAST ONE POLYMER PARTICLE DISPERSED IN AT LEAST ONE LIQUID FATTY PHASE AND AT LEAST ONE ESTER OF AT LEAST ONE ACID AND AT LEAST ONE POLYOL ESTER

(75) Inventors: Xavier Blin, Paris (FR); Caroline Lebre, Thiais (FR)

(73) Assignee: L'Oreal S.A., Paris (FR)

( * ) Notice: Subject to any disclaimer, the term of this patent is extended or adjusted under 35 U.S.C. 154(b) by 215 days.

(21) Appl. No.: 12/004,050

(22) Filed: Dec. 20, 2007

(65) Prior Publication Data

US 2008/0107697 A1 May 8, 2008

Related U.S. Application Data

(63) Continuation of application No. 10/784,948, filed on Feb. 25, 2004, now abandoned.

(60) Provisional application No. 60/452,066, filed on Mar. 10, 2003.

(30) Foreign Application Priority Data

Feb. 25, 2003 (FR) ...................... 03 50034

(51) Int. Cl.
*A61K 8/02* (2006.01)
(52) U.S. Cl. ........................................ 424/401
(58) Field of Classification Search .................. 424/401, 424/450
See application file for complete search history.

(56) References Cited

U.S. PATENT DOCUMENTS

| | | | |
|---|---|---|---|
| 4,152,416 A | 5/1979 | Spitzer et al. | |
| 5,221,534 A | 6/1993 | DesLauriers et al. | |
| 5,945,095 A | 8/1999 | Mougin et al. | |
| 6,074,654 A | 6/2000 | Drechsler et al. | |
| 6,120,781 A | 9/2000 | Le Bras et al. | |
| 6,132,742 A | 10/2000 | Le Bras et al. | |
| 6,361,782 B1 * | 3/2002 | Chevalier et al. | 424/401 |
| 6,395,701 B1 * | 5/2002 | Connor et al. | 510/437 |
| 2003/0021756 A1 | 1/2003 | Ferrari | |
| 2003/0039621 A1 | 2/2003 | Arnaud et al. | |
| 2004/0018163 A1 | 1/2004 | Yu | |
| 2004/0137028 A1 | 7/2004 | de la Poterie | |
| 2004/0156804 A1 | 8/2004 | Poterie et al. | |

FOREIGN PATENT DOCUMENTS

| | | |
|---|---|---|
| EP | 0 667 146 B1 | 8/1995 |
| EP | 0 749 746 B1 | 12/1996 |
| EP | 1 002 528 B1 | 5/2000 |
| EP | 1 034 776 A1 | 9/2000 |
| EP | 1 044 673 A1 | 10/2000 |
| EP | 1161937 A2 * | 12/2001 |
| EP | 1 249 223 A1 | 10/2002 |
| EP | 1 262 164 A1 | 12/2002 |
| FR | 2 794 970 A1 | 12/2000 |
| WO | WO 02/67877 A2 | 9/2002 |

OTHER PUBLICATIONS

English translation of EP 1,161,937 A2, Banowski et al. (2001).*
English-translation of EP 1161937 A1, Banowski et al. (enclosed abstract). (Dec. 2001).*
French Search Report for FR 03 50034, dated Jan. 30, 2004.
English language Derwent Abstract of EP 1 034 776 A1, Sep. 13, 2000.

* cited by examiner

*Primary Examiner* — Kevin E Weddington
(74) *Attorney, Agent, or Firm* — Finnegan, Henderson, Farabow, Garrett & Dunner, LLP

(57) ABSTRACT

The present disclosure, in one embodiment, relates to a cosmetic composition for caring for or making up the skin and/or epidermal derivatives and/or lips, which comprises a physiologically acceptable medium comprising a) at least one liquid fatty phase, b) a dispersion of at least one polymer particle dispersed in the at least one liquid fatty phase, and c) at least one ester of at least one carboxylic acid comprising 1 to 7 carbons and at least one polyol comprising at least 4 hydroxyl groups, the at least one ester having a molecular mass of less than 5,000 g/mol. This composition allows a film to be obtained on the skin, epidermal derivatives or lips which does not undergo transfer, has good staying power and goes on easily.

62 Claims, No Drawings

COSMETIC COMPOSITION COMPRISING AT LEAST ONE POLYMER PARTICLE DISPERSED IN AT LEAST ONE LIQUID FATTY PHASE AND AT LEAST ONE ESTER OF AT LEAST ONE ACID AND AT LEAST ONE POLYOL ESTER

This is a continuation of application Ser. No. 10/784,948, filed Feb. 25, 2004 now abandoned, which claims the benefit of priority of French Patent Application No. 03 050034, filed Feb. 25, 2003, and which also claims the benefit of U.S. Provisional Application No. 60/452,066, filed Mar. 10, 2003, all of which are incorporated herein by reference.

The present disclosure concerns a composition intended, for example, for the cosmetics field, comprising polymer particles dispersed in a liquid fatty phase, wherein the at least one polymer particle is, for example, surface-stabilized in the at least one liquid fatty phase by at least one stabilizer. This composition may further comprise at least one ester of an acid and at least one polyol, such as a sucrose ester.

The disclosure relates, in one embodiment, to a composition for caring for or making up keratin materials, such as the skin both of the face and of the human body, including the scalp, the epidermal derivatives such as the eyelashes, eyebrows, nails and hair, and also the lips and upper or lower eyelids of human beings.

The composition of the disclosure may provide access to makeup with staying power which does not undergo transfer and/or is easy to apply.

Non-transfer or no-transfer compositions are compositions which on a substrate form a deposit which does not undergo deposition at least in part onto articles (glasses, clothes, cigarettes) with which the compositions are brought into contact.

A makeup with staying power is one whose colour and/or gloss lasts throughout the day and which is resistant to trials, in particular to eating in the case of a lipstick.

In one embodiment, the composition is easy to apply, in the sense that it goes on smoothly and spreads readily, and/or in the sense that the mass thereof deposited in one pass gives a satisfactory makeup result.

According to one of its aspects, the present disclosure relates to a cosmetic product comprising at least two compositions which are applied in succession, in particular to the skin, lips or epidermal derivatives, the first composition comprising a) at least one liquid fatty phase and b) a dispersion of at least one polymer particle dispersed in the at least one liquid fatty phase, and c) at least one ester of at least one carboxylic acid comprising from 1 to 7 carbon atoms and at least one polyol comprising at least 4 hydroxyl groups, the at least one ester having a molecular mass of less than 5,000 g/mol and the second composition comprising a physiologically acceptable medium.

Known non-transfer compositions (U.S. Pat. No. 6,074,654, WO 02/067877) are generally based on silicone resins and volatile silicone oils and, although having improved staying properties, may have the disadvantage of leaving on the skin and lips, following evaporation of the volatile silicone oils, a film which becomes uncomfortable over time (sensation of drying and tightening), which distances a certain number of women from this type of product.

In order to remedy these disadvantages, the inventor conceived of the manufacture of makeup compositions comprising polymer particles dispersed and surface-stabilized by a stabilizer in a liquid fatty phase, such as those described in EP 1 249 223 (L'Oréal).

In one embodiment, the present invention provides a makeup product which has improved non-transfer and/or staying properties, while retaining good cosmetic qualities.

The inventor has found surprisingly that combining a particular acid and at least one polyol ester with a fatty phase comprising a polymer particle dispersion may give a makeup which has good staying power and/or does not undergo transfer, while going on smoothly.

For example, in one embodiment, the product of the disclosure may provide access to continuous, non-tacky deposits which exhibit good coverage, do not migrate and do not dry out the skin or lips to which they are applied, either during application or over time. The product may also feature good application properties: the deposit dries rapidly and the colour is deposited correctly in a single pass. The product may also allow a natural makeup result to be obtained, with well-defined contours, which leaves a sensation of bare lips, in contrast to the prior art compositions, during the deposition of which the consumer is aware of her lips retracting, of unattractive emphasizing of the lip microrelief, and of a sensation of drying.

The inventor has also found that the product of the disclosure may have the advantageous qualities of spreading and of adhesion to the skin, lips, eyelashes or mucosae, and also a pleasant and creamy feel.

In one embodiment, its properties of staying power, transfer resistance and migration resistance make it a product which is suitable for producing makeup products for the face, for example, for the lips, such as lipstick and lipgloss, or the eyes, such as mascara, eyeliner or eyeshadow, or the skin, such as foundation.

The disclosure applies not only to lip makeup products but may also apply to products for caring for and/or treating the lips, such as lip balm, and the skin including the scalp, such as facial sun protection and daycare creams, to skin makeup products, both for the face and for the human body, such as foundations, particularly those cast in the form of sticks or dishes, concealer products and temporary tattooing products, to body hygiene products such as deodorants, such as stick deodorants, and to eye makeup products, such as eyeliners, for example, in pencil form, and mascaras, such as in cake form.

DEFINITIONS

A liquid fatty phase for the purposes of the application is any non-aqueous medium which is liquid at ambient temperature (25° C.) and atmospheric pressure (760 mm Hg) and is composed of at least one fatty substance which is liquid at ambient temperature, also called oil, with the exception of an ester formed from acid and at least one polyol, and also gelling agents and stabilizers for pigments optionally present in the composition, provided that they are liquid at ambient temperature and atmospheric pressure. This fatty phase may comprise a volatile liquid fatty phase and/or a non-volatile fatty phase.

A non-volatile fatty phase is any medium apt to remain on the skin or lips without evaporating. A non-volatile fatty phase has in particular a non-zero vapour pressure at ambient temperature and atmospheric pressure, of less than 0.02 mm Hg and, such as less than $10^{-3}$ mm Hg.

A volatile fatty phase is any non-aqueous medium apt to evaporate from the skin or lips at ambient temperature and atmospheric pressure. This volatile phase comprises, in particular, oils having a vapour pressure at ambient temperature (25° C.) and atmospheric pressure (760 mm Hg) ranging from $10^{-3}$ to 300 mm Hg (0.13 Pa to 40,000 Pa), for example, ranging from 0.02 to 300 mm Hg (2.66 Pa to 40,000 Pa).

The term "goniochromatic" means able to produce different colors depending on the light incidence and viewing angle.

The term "hydrocarbon oil" refers to oils comprising primarily carbon atoms and hydrogen atoms, for example, alkyl or alkenyl chains, such as alkanes or alkenes, but also oils comprising an alkyl or alkenyl chain comprising at least one group chosen from ethers, esters and carboxylic acids.

The term "substantially free" means not more than trace amounts or impurities.

The term "substituted" means further comprising at least one substituent chosen from an oxygen, nitrogen or halogen atom and a hydroxyl, ether, oxyalkylene, polyoxyalkylene, carboxyl, amine and amide group.

The term "saccharide" refers to a monosaccharide or a polysaccharide.

"Polar groups" are well known to the person skilled in the art; they may be, for example, ionic or non-ionic polar groups selected from —COOH; —OH; ethylene oxide; propylene oxide; —$PO_4$; —NHR; —$NR_1R_2$, wherein $R_1$ and $R_2$, which may be identical or different, may form a ring and are chosen from linear and branched $C_1$ to $C_{20}$ alkyl and alkoxy radicals.

A gelling agent is a compound which increases the viscosity of the medium into which it is incorporated or which stiffens the said medium. The gelling agent according to the invention does not include waxes.

A wax is for the purposes of the present invention a lipophilic fatty compound which is solid at ambient temperature (25° C.) and exhibits a reversible solid/liquid state change, the compound having a melting temperature of greater than 40° C. and possibly up to 200° C. and having an anisotropic crystalline organization in the solid state. The size of the crystals is such that they diffract and/or scatter light, thereby endowing the composition with a turbid, opaque appearance. By bringing the wax to its melting temperature it can be made miscible with the oils and made to form a microscopically homogeneous mixture; however, by bringing the temperature of the mixture back to ambient temperature, the wax is recrystallized in the oils of the mixture. In one embodiment, it is this recrystallization in the mixture which is responsible for the decrease in the gloss of the said mixture.

SUMMARY OF THE INVENTION

The present disclosure provides a cosmetic composition intended for application to keratin materials, comprising a) at least one liquid fatty phase, b) a dispersion of at least one polymer particle dispersed in the at least one liquid fatty phase, and c) at least one ester of at least one carboxylic acid comprising from 1 to 7 carbons atoms and at least one polyol comprising at least 4 hydroxyl groups, the at least one ester having a molecular mass of less than 5 000 g/mol.

The disclosure further provides for the use of an ester of at least one acid comprising 1 to 7 carbon atoms and at least one polyol comprising at least 4 hydroxy groups, the ester having a molecular mass of less than 5,000 g/mol in a composition intended for application to the skin, the lips and the epidermal derivatives, the composition being cosmetic or hygienic, or for preparing a dermatological or pharmaceutical composition for application to the skin, lips and epidermal derivatives, the composition comprising particles of at least one polymer, dispersed in a liquid fatty phase—in order to limit the transfer of the composition and/or to increase its staying power over time and/or to enhance its deposition.

The disclosure additionally provides a cosmetic method of caring for or making up keratin materials, such as the lips, epidermal derivatives or skin, which comprises applying to the lips, epidermal derivatives or skin a cosmetic composition as defined above.

The disclosure further provides a method of limiting the transfer of a lip or skin care or makeup composition and/or increasing its staying power over time and/or facilitating its application, comprising applying to the skin or lips a composition, wherein the composition comprises a liquid fatty phase and polymer particles dispersed in the fatty phase, the method comprising introducing into the liquid fatty phase at least one ester of at least one acid comprising from 1 to 7 carbon atoms and at least one polyol comprising at least 4 hydroxyl groups, the ester having a molecular mass of less than 5,000 g/mol.

The disclosure additionally provides a method of producing a composition intended for application to keratin materials, comprising introducing into a physiologically acceptable liquid medium a) a dispersion of polymer particles in a liquid fatty phase and b) at least one ester of at least one acid comprising 1 to 7 carbon atoms and at least one polyol comprising at least 4 hydroxyl groups, the ester having a molecular mass of less than 5,000 g/mol.

Acid and Polyol Ester

The composition according to the disclosure comprises at least one ester of at least one carboxylic acid comprising from 1 to 7 carbon atoms and of at least one polyol comprising at least 4 hydroxyl groups, the ester having a molecular mass of less than 5,000 g/mol.

The at least one ester may have, for example, a molecular mass of less than 2,000, for further example, less than 1,000, such as less than 900 g/mol. The molecular mass of the at least one ester may be, for example, greater than 100 g/mol.

The polyol according to the disclosure may be a monosaccharide—a polyhydroxyaldehyde (aldose) or polyhydroxyketone (ketose)—which may be cyclized or not. The polyol may be, for example, a monosaccharide cyclized in hemiacetal form.

The at least one polyol may also be a polyol derived from a monosaccharide, such as eythritol, xylitol or sorbitol.

Among aldoses mention may be made of D-ribose, D-xylose, L-arabinose, D-glucose (or alpha-D-glucopyranose when in cyclic hemiacetal form), D-mannose and D-galactose.

Among ketoses mention may be made of D-xylulose and D-fructose (or beta-D-fructofuranose when in cyclic hemiacetal form).

The polyol may be a monosaccharide or a polysaccharide comprising from 1 to 10 monosaccharide units, for example, from 1 to 4, such as 1 or 2 monosaccharide units.

The polyol may be chosen from, for example, erythritol, xylitol, sorbitol, glucose and sucrose.

The polyol according to the disclosure may be, for instance, a disaccharide. Among disaccharides mention may be made of sucrose (alpha-D-glucopyranosyl-(1-3)-beta-D-fructofuranose), lactose (beta-D-galactopyranosyl-1(1-4)-beta-D-glucopyranose) and maltose (alpha-D-glucopyranosyl-(1-4)-beta-D-glucopyranose).

The polyol may be a polysaccharide comprising two or more identical monosaccharide units or at least two different monosaccharide units. The ester disclosed herein may be comprised of at least one polyol substituted by at least two different monocarboxylic acids or by at least three different monocarboxylic acids.

The at least one ester may be obtained by polymerising two esters according to the invention, in particular by polymerising i) a sucrose substituted by benzoyl groups and ii) a sucrose substituted by a group chosen from acetyls and isobutyryls.

The at least one ester may comprise, for example, no polar group, such as no hydroxyl group. In other words, during the esterification reaction between the acid and the polyol, the acid is added in an amount sufficient to react with all of the hydroxyl groups of the polyol. The polar groups may be, for example, ionic or non-ionic polar groups chosen from —COOH; —OH; ethylene oxide; propylene oxide; —PO$_4$; —NHR; —NR$_1$R$_2$ with R$_1$ and R$_2$, which may be identical or different, optionally forming a ring and chosen from linear and branched C$_1$ to C$_{20}$ alkyl and alkoxy radicals.

The acid may be, for example, a monocarboxylic acid comprising from 1 to 7 carbon atoms, for example, 1 to 5 carbon atoms. It may be chosen from, for example, acetic, n-propanoic, isopropanoic, n-butanoic, isobutanoic, tert-butanoic, n-pentanoic and benzoic acids.

The at least one ester may be obtained from at least two different monocarboxylic acids.

In one non-limiting embodiment the acid is chosen from unsubstituted linear and branched acids.

The acid may be chosen from, for example, acetic acid, isobutyric acid and benzoic acid.

In one non-limiting embodiment the ester may be sucrose diacetate hexa(2-methylpropanoate).

The ester may be, for example, liquid at ambient temperature and atmospheric pressure. It is advantageously present in an amount ranging from 0.1 to 25% by weight, for example, from 0.5 to 15% by weight, such as from 3 to 15% by weight.

The mass ratio between the polymer particles and the acid and polyol ester is advantageously from 0.5 to 100, for example, from 1 to 50, for further example, from 1 to 10, such as from 1 to 5.

Polymer Particles in Dispersion

The at least one polymer particle disclosed herein may be a solid which is insoluble in the liquid organic phase of the first composition even at its softening temperature, in contradistinction to a wax, even a wax of polymeric origin, which is soluble in the liquid organic phase (or fatty phase) at its melting temperature. In addition, it may allow the formation of a deposit, such as a film-forming deposit, which may be continuous and homogeneous and/or is characterized by the interpenetration of the polymeric chains. With a wax, even one obtained by polymerization, melting in the liquid organic phase may be followed by recrystallization. It is this recrystallization which may be responsible, for the loss of gloss of the composition.

In one embodiment, to optimize the non-transfer properties the amount of polymer particles is selected as a function of the amount of colorants and/or actives and/or oils present in the first composition. As disclosed herein the amount of polymer particles may be greater than 5% by weight (in terms of active substance) relative to the total weight of the composition.

In one embodiment, a dispersion of polymer particles is used in the composition disclosed herein because these particles remain in the state of elementary particles, without forming agglomerates, in the fatty phase. The polymer particle dispersion may also provide the possibility of obtaining highly fluid compositions (of the order of 130 centipoises), even in the presence of a high proportion of polymer.

When using a polymer dispersion of this kind, the polymer particle size may be calibrated at will and their size "polydispersity" modified during the synthesis. It may be possible to obtain very small-sized particles which are invisible to the naked eye when in the composition and when applied to the skin, lips or epidermal derivatives.

One composition of the product of the disclosure may comprises at least one stable dispersion of polymer particles, generally spherical particles, of at least one polymer particle in a physiologically acceptable liquid organic phase. These dispersions may, for example, be in the form of polymer nanoparticles in stable dispersion in the liquid organic phase. The nanoparticles may be of an average size, for example, ranging from 5 to 800 nm, such as from 50 to 500 nm. It is possible, however, to obtain polymer particle sizes ranging up to 1 µm.

The at least one polymer particle in dispersion may be, for example, insoluble in water-soluble alcohols such as ethanol, for example.

The at least one polymer particle in dispersion that may be used in the first composition of the invention may have, for example, a molecular weight ranging from 2,000 to 10,000,000 g/mol.

It is possible to use filmable polymer particles, such as those having a low glass transition temperature, $T_g$, for example, less than or equal to the temperature of the skin, such as less than or equal to 40° C.

The at least one polymer particle used may be filmable, that is, it is able, alone or in combination with a plasticizer, to form an isolatable film. It is also possible to use a non-filmable polymer particle.

A non-filmable polymer particle is a polymer particle which is not capable on its own of forming an isolatable film. In combination with a non-volatile compound of the oil type, this polymer particle allows a continuous and homogeneous deposit to be formed on the skin and/or lips.

Among filmable polymer particles mention may be made of radical, acrylic or vinyl homopolymers or copolymers, such as those having a $T_g$ of less than or equal to 40° C., for example, ranging from −10° C. to 30° C., which are used alone or in a mixture.

Among non-filmable polymer particles mention may be made of radical, vinyl or acrylic homopolymers or copolymers, optionally crosslinked, such as those having a $T_g$ of greater than 40° C., for example, ranging from 45° C. to 150° C., which are used alone or in a mixture.

A radical polymer is a polymer obtained by polymerizing monomers comprising unsaturation, for example, ethylenic unsaturation, each monomer being capable of undergoing homopolymerization (in contrast to polycondensates). The radical polymers may be, for example, vinyl polymers or copolymers, such as acrylic polymers.

The acrylic polymers may result from the polymerization of ethylenically unsaturated monomers having at least one acid group and/or esters of these acid monomers and/or amides of these acids.

As a monomer carrying an acid group it is possible to use α,β-ethylenic unsaturated carboxylic acids such as acrylic acid, methacrylic acid, crotonic acid, maleic acid and itaconic acid. For example, (Meth)acrylic acid and crotonic acid may be used, and, for further example, (meth)acrylic acid.

The esters of acid monomers may be chosen from esters of (meth)acrylic acid (also called (meth)acrylates), such as alkyl (meth)acrylates, for example, $C_1$-$C_{20}$, such as $C_1$-$C_8$, alkyl (meth)acrylates, aryl(meth)acrylates, for example, $C_6$-$C_{10}$ aryl(meth)acrylates, and hydroxyalkyl(meth)acrylates, for example, $C_2$-$C_6$ hydroxyalkyl(meth)acrylates. Alkyl(meth) acrylates include methyl, ethyl, butyl, isobutyl, 2-ethylhexyl and lauryl(meth)acrylate. Hydroxyalkyl(meth)acrylates include hydroxyethyl(meth)acrylate and 2-hydroxypropyl (meth)acrylate. Aryl(meth)acrylates include benzyl acrylate and phenyl acrylate.

For example, the esters of (meth)acrylic acid such as the alkyl (meth)acrylates may be used.

As the radical polymer copolymers of (meth)acrylic acid and alkyl (meth)acrylate, such as $C_1$-$C_4$ alkyl(meth)acrylate, may be used. For example, It is possible to use methyl acrylates optionally copolymerized with acrylic acid.

Amides of the acid monomers include (meth)acrylamides, for example, N-alkyl(meth)acrylamides, for further example, N—$C_2$-$C_{12}$-alkyl(meth)acrylamides, such as N-ethylacrylamide, N-t-butylacrylamide and N-octylacrylamide, and N-di ($C_1$-$C_4$)alkyl(meth)acrylamides.

The acrylic polymers may result from the polymerization of ethylenically unsaturated monomers having at least one amine group, in free form or else in partly or totally neutralized form, or else in partly or totally quaternized form. Such monomers may be, for example, dimethylaminoethyl(meth)acrylate, dimethylaminoethylmethacrylamide, vinylamine, vinylpyridine or diallyldimethylammonium chloride.

The vinyl polymers may result from the homopolymerization or copolymerization of at least one monomer chosen from vinyl esters and styrenic monomers. For example, these monomers may be polymerized with acid monomers and/or their esters and/or their amides, such as those mentioned above. Non-limiting examples of vinyl esters include vinyl acetate, vinyl propionate, vinyl neodecanoate, vinyl, pivalate, vinyl benzoate and vinyl t-butylbenzoate. Styrenic monomers include, for example, styrene and alpha-methylstyrene.

The list of monomers given is not limiting and it is possible to use any monomer known to the person skilled in the art which falls within the categories of acrylic monomers and vinyl monomers (including monomers modified with a silicone chain).

As other vinyl monomers which may be used non-limiting mention may also be made of the following:

N-vinylpyrrolidone, vinylcaprolactam, vinyl-N—($C_1$-$C_6$) alkylpyrroles, vinyloxazoles, vinylthiazoles, vinylpyrimidines and vinylimidazoles; and olefins such as ethylene, propylene, butylene, isoprene and butadiene.

The vinyl polymer may be crosslinked using at least one difunctional monomer, comprising, for example, at least two ethylenic unsaturations, such as ethylene glycol dimethacrylate or diallyl phthalate.

Without limitation, the polymer particles in dispersion disclosed herein may be chosen from the following polymers and copolymers: polyurethanes, acrylic polyurethanes, polyureas, polyurea-polyurethanes, polyester-polyurethanes, polyether-polyurethanes, polyesters, polyester amides, fatty-chain polyesters, alkyds; acrylic and/or vinyl polymers or copolymers; acrylic-silicone copolymers; polyacrylamides; silicone polymers such as silicone polyurethanes or silicone acrylics, fluorinated polymers, and mixtures thereof.

The at least one polymer particle in dispersion in the organic liquid phase may range from 5 to 40% by weight of the dry-matter content of the composition, for example, from 5 to 35% such as from 8 to 30%.

In one non-limiting embodiment the polymer particles in dispersion are surface-stabilized by at least one stabilizer which is solid at ambient temperature. In that case the amount of the dispersion in terms of dry matter represents the total amount of polymer and stabilizer subject to the proviso that the amount of polymer in terms of dry matter may not be less than 5%.

One choice is to use a dispersion of filmable polymer particles, the particles being dispersed in a volatile oil.

Polymer Particle Stabilization

In some embodiments, the polymer particles may be surface-stabilized by means of at least one stabilizer which may be chosen from block polymers, graft polymers, and random polymers, such as, for example, a mixture of any of these.

Stabilization can be effected by any known means, for example, by direct addition of the block polymers, graft polymers and/or random polymers during the polymerization.

The at least one stabilizer may also be present, for example, in the mixture before polymerization of the polymer. However, it is also possible to add it continuously, such as when the monomers are also added continuously.

The at least one stabilizer may be used in an amount ranging from 2 to 30% by weight, relative to the initial mixture of monomers, such as from 5 to 20% by weight.

In one embodiment, when a graft polymer and/or block polymer is used as the stabilizer, the synthesis solvent is chosen such that at least some of the grafts or blocks in the stabilizing polymer are soluble in the solvent, and the remainder of the grafts or blocks are not soluble therein. The stabilizing polymer used during the polymerisation should be soluble or dispersible in the synthesis solvent. Furthermore, at least one stabilizer may be chosen whose insoluble blocks or grafts have a certain affinity for the polymer formed during the polymerization.

Among graft polymers mention may be made of silicone polymers grafted with a hydrocarbon chain and hydrocarbon polymers grafted with a silicone chain.

Thus, block or graft block copolymers comprising at least one block of polyorganosiloxane type and at least one block of a radical polymer can be used, such as graft copolymers of acrylic/silicone type, which can be used, for example, when the non-aqueous medium is silicone-based.

It is also possible to use block or graft block copolymers comprising at least one block of polyorganosiloxane type and at least one polyether. The polyorganopolysiloxane block can be, for example, a polydimethylsiloxane or alternatively a poly($C_2$-$C_{18}$)-alkylmethylsiloxane; the polyether block can be a poly($C_2$-$C_{18}$)alkylene, such as those chosen from polyoxyethylene and polyoxypropylene. For example, it is possible to use dimethicone copolyols or ($C_2$-$C_{18}$)alkyldimethicone copolyols such as those sold under the name Dow Corning 3225C by the company Dow Corning, and lauryl methicones such as those sold under the name Dow Corning Q2-5200 by the company Dow Corning.

Block or graft block copolymers which may also be mentioned are those comprising at least one block resulting from the polymerization of at least one ethylenic monomer comprising at least one optionally conjugated ethylenic bond, such as ethylenes and dienes such as butadiene and isoprene, and at least one block of a vinyl polymer such as a styrenic polymer. When the ethylenic monomer comprises two or more optionally conjugated ethylenic bonds, the residual ethylenic unsaturations after the polymerization are generally hydrogenated. Thus, in a known manner, the polymerization of isoprene leads, after hydrogenation, to the formation of an ethylene-propylene block, and the polymerization of butadiene leads, after hydrogenation, to the formation of an ethylene-butylene block. Among these polymers mention may be made of block copolymers, for example, diblock and triblock copolymers such as polystyrene/polyisoprene (SI), polystyrene/polybutadiene (SB), such as those sold under the name Luvitol HSB by BASF, polystyrene/copoly(ethylene-propylene) (SEP), such as those sold under the name Kraton by Shell Chemical Co., or alternatively polystyrene/copoly(ethylene-butylene) (SEB). In particular, Kraton G1650 (SEBS), Kraton G1651 (SEBS), Kraton G1652 (SEBS), Kraton G1657X (SEBS), Kraton G1701X (SEP), Kraton G1702X (SEP), Kraton G1726X (SEB), Kraton D-1101 (SBS), Kraton D-1102 (SBS) and Kraton D-1107 (SIS) may be used. The polymers are generally referred to as copolymers of hydrogenated or non-hydrogenated dienes.

Gelled Permethyl 99A-750, 99A-753-59 and 99A-753-58 (mixture of triblock polymer and star polymer), Versagel 5960 from Penreco (triblock polymer+star polymer), and OS129880, OS129881 and OS84383 from Lubrizol (styrene/methacrylate copolymer) can also be used.

As block or graft block copolymers comprising at least one block resulting from the polymerization of at least one ethylenic monomer comprising at least one ethylenic bond and at least one block of an acrylic polymer, mention may be made of poly(methyl methacrylate)/polyisobutylene diblock and triblock copolymers and graft copolymers comprising a poly(methyl methacrylate) backbone and polyisobutylene grafts.

As block or graft block copolymers comprising at least one block resulting from the polymerization of at least one ethylenic monomer comprising at least one ethylenic bond and at least one block of a polyether such as a $C_2$-$C_{18}$ polyalkylene (in particular polyethylenated and/or polyoxypropylenated), mention may be made of polyoxyethylene/polybutadiene and polyoxyethylene/polyisobutylene diblock and triblock copolymers.

In another embodiment, when a random polymer is used as a stabilizer, it is selected such that it has a sufficient amount of groups making it soluble in the intended synthesis solvent.

It is thus possible to use copolymers based on alkyl acrylates or methacrylates derived from $C_1$-$C_4$ alcohols and alkyl acrylates or methacrylates derived from $C_8$-$C_{30}$ alcohols. Mention may be made, for example, of stearyl methacrylate/methyl methacrylate copolymer.

In one embodiment, when the polymer synthesis solvent is apolar, a polymer may be chosen, for example, which gives the most complete coverage possible of the particles, a plurality of stabilizing polymer chains then being adsorbed onto a polymer particle obtained by polymerization.

In this case, either a graft polymer or a block polymer may be used, for example, as a stabilizer, so as to have better interfacial activity. The reason for this may be that blocks or grafts which are insoluble in the synthesis solvent give a more voluminous coverage at the surface of the particles.

When the liquid synthesis solvent comprises at least one silicone oil, the stabilizer may be chosen from the group consisting of block and graft block copolymers comprising at least one block of polyorganosiloxane type and at least one block chosen from a radical polymer, polyether, and polyester such as polyoxypropylenated and/or oxyethylenated blocks.

When the at least one liquid fatty phase comprises no silicone oil, the at least one stabilizer may be selected from the group consisting of:

(a) block and graft block copolymers comprising at least one block of polyorganosiloxane type and at least one block chosen from radical polymers, polyethers, and polyesters, (b) copolymers of alkyl acrylates and methacrylates derived from $C_1$-$C_4$ alcohols, and of alkyl acrylates and methacrylates derived from $C_8$-$C_{30}$ alcohols, (c) block and graft block copolymers comprising at least one block resulting from the polymerization of at least one ethylenic monomer comprising conjugated ethylenic bonds, and at least one block chosen from vinyl polymers, acrylic polymers, polyethers, polyesters, and mixtures thereof.

Diblock polymers may be used, for example, as a stabilizer.

Fatty Phase

The at least one liquid fatty phase of the composition may, for example, be comprised of any cosmetically or dermatologically acceptable, and more generally physiologically acceptable, oil, selected, for example, from oils of mineral, vegetable or synthetic origin, including carbon-based oils, hydrocarbon oils, fluoro oils and/or silicone oils, alone or in a mixture, insofar as they form a homogeneous and macroscopically stable mixture and as they are compatible with the intended The total liquid fatty phase of the composition may range from 5 to 90% of the total weight of the composition, for example, from 20 to 85%. Advantageously, it represents at least 30% of the total weight of the composition. This fatty phase may comprise, for example, at least one volatile oil.

Volatile Oils of the Fatty Phase

In one embodiment, the composition comprises at least one volatile oil.

These oils, for example, may be hydrocarbon oils and silicone oils optionally comprising groups chosen from alkyl groups and alkoxy groups, pendantly or at the end of the silicone chain.

As the volatile silicone oils disclosed herein mention may be made of linear and cyclic silicones having a viscosity at ambient temperature of less than 8 cSt and having, for example, 2 to 7 silicon atoms, these silicones optionally comprising groups chosen from alkyl groups and alkoxy groups having 1 to 10 carbon atoms. As volatile silicone oils which can be used in the disclosure mention may be made, for example, of octamethylcyclotetrasiloxane, decamethylcyclopentasiloxane, dodecamethylcyclohexasiloxane, heptamethylhexyltrisiloxane, heptamethyloctyltrisiloxane, octamethyltrisiloxane, decamethyltetrasiloxane and mixtures thereof.

Other volatile oils which can be used in the disclosure include, for example, $C_8$-$C_{16}$ isoalkane oils (also called isoparaffins) such as isododecane, isodecane, isohexadecane and, for example, the oils sold under the trade names Isopar and Permethyl, and in particular isododecane (Permethyl 99A).

The volatile oils range from 5 to 85% of the total weight of the composition, for example, from 20 to 75%.

Synthesis Solvent of the Polymer Particles

The polymer dispersion may be prepared as described in EP-A-749 747.

In one embodiment, a mixture is prepared comprising the initial monomers and a free-radical initiator. This mixture is dissolved in a solvent which, for the remainder of the present disclosure, is referred to as the "synthesis solvent". When the fatty phase is a non-volatile oil, the polymerization may be carried out in an apolar organic solvent (synthesis solvent) and then the non-volatile oil (which must be miscible with the synthesis solvent) is added and the synthesis solvent is distilled off selectively.

A synthesis solvent may be selected such that the initial monomers and the free-radical initiator are soluble therein and the polymer particles obtained are insoluble therein, so that they precipitate from the solvent as they are formed. The synthesis solvent may, for example, be chosen from alkanes such as heptane, isododecane and cyclohexane.

When the at least one fatty phase selected is a volatile oil the polymerization may be carried out directly in the oil, which hence also acts as the synthesis solvent. The monomers must also be soluble therein, and the free-radical initiator too, and the polymer obtained must be insoluble therein.

The monomers are, for example, present in the synthesis solvent, prior to polymerization, in an amount ranging from 5 to 20% by weight of the reaction mixture. The total amount of the monomers may be present in the solvent before the beginning of the reaction, or a fraction of the monomers may be added at the rate at which the polymerization reaction proceeds.

The free-radical initiator may be, for example, azobisisobutyronitrile or tert-butyl peroxy-2-ethylhexanoate.

The volatile phase of the composition may comprise the synthesis solvent of the dispersed polymer particles.

Non-Volatile Oil of the at Least One Fatty Phase

The at least one fatty phase may comprise at least one oil chosen from apolar and relatively non-polar non-volatile oil.

As relatively non-polar non-volatile oils which can be used in the disclosure mention may be made of apolar oils and, for example, oils comprising an alkyl chain such as a $C_3$-$C_{40}$ alkyl chain. Examples of apolar and relatively non-polar oils include the following:

linear and branched hydrocarbons such as liquid paraffin, vaseline oil and light naphthalene oil and hydrogenated polyisobutene;

hydrocarbon oils of animal origin such as squalene;

vegetable hydrocarbon oils such as the liquid triglycerides of fatty acids of at least 10 carbon atoms;

synthetic esters and ethers, for example, those of fatty acids, such as the oils of formula $R_1(CO)_xOR_2$ wherein $R_1$ is the residue of an acid comprising 2 to 29 carbon atoms; x is 0 or 1, and $R_2$ is a hydrocarbon chain comprising 3 to 30 carbon atoms, such as, for example, tributyl acetylcitrate, oleyl erucate, 2-octyldodecyl behenate, triisoarachidylcitrate, isocetyl stearoylstearate or octyldodecanyl stearoylstearate, n-propyl acetate, tridecyl trimellitate, dodecane dioleate or diisocetyl stearate, arachidyl propionate, dibutyl phthalate, propylene carbonate and octyldodecyl pentanoate; polyol esters such as vitamin F, sorbitan isostearate, glyceryl triisostearate and diglycerol;

silicone oils such as polydimethylsiloxanes (PDMS), optionally comprising a chain chosen from $C_3$-$C_{40}$ alkyl, $C_3$-$C_{40}$ alkoxy, and a phenyl chain, such as phenyltrimethicones, polyalkylmethylsiloxanes, optionally fluorinated such as the polymethyltrifluoropropyldimethylsiloxanes, or optionally with functional groups such as hydroxyl, thiol and amine groups; and polysiloxanes modified with at least one of fatty acids, fatty alcohols and polyoxyalkylenes;

fluoro oils;

mixtures thereof.

These non-volatile apolar or relatively non-polar oils may range from 0.1 to 20% of the total weight of the composition, for example, from 0.5 to 10%, such as from 1 to 5% of the total weight of the composition.

The non-volatile oil may be, for example, apolar. It is advantageously chosen from hydrocarbons, for example, alkanes, such as hydrogenated polyisobutene.

The at least one fatty phase may further comprise a polar oil chosen from fatty acid esters of 7 to 29 carbon atoms such as diisostearyl malate, isopropyl palmitate, diisopropyl adipate, the triglycerides of caprylic/capric acids, such as those sold by Stearineries Dubois or those sold under the names Miglyol 810, 812 and 818 by Dynamit Nobel, the oil of shea butter, isopropyl myristate, butyl stearate, hexyl laurate, diisopropyl adipate, isononyl isononanoate, 2-hexyldecyl laurate, 2-octyldecyl palmitate, 2-octyldodecyl myristate or lactate, di-2-ethylhexyl succinate, 2-ethylhexyl palmitate, 2-octyldodecyl stearate, castor oil; esters of lanolic acid, lauric acid and stearic acid; higher fatty alcohols (of 7 to 29 carbon atoms) such as stearyl alcohol, linoleyl alcohol or linolenyl alcohol, isostearyl alcohol, 2-octyldodecanol, decanol, dodecanol, octadecanol or oleyl alcohol; higher fatty acids (of 7 to 29 carbon atoms) such as myristic acid, palmitic acid, stearic acid, behenic acid, oleic acid, linoleic acid, linolenic acid or isostearic acid; and mixtures thereof.

These non-volatile polar oils may range from 0.1 to 10% of the total weight of the composition such as from 1 to 5%.

In one non-limiting embodiment of the disclosure the least one liquid fatty phase comprises at least one apolar volatile oil and at least one apolar non-volatile oil.

Gelling Agent

In one embodiment of the disclosure the composition may comprise a gelling agent for the at least one liquid fatty phase, the agent being chosen from a polymeric and mineral gelling agent.

The gelling agent increases the viscosity of the at least one liquid fatty phase or stiffens it. The gelling agent according to the present disclosure does not embrace waxes.

The gelling agent may be chosen from ethylene homopolymers and copolymers whose weight-average molecular mass ranges from 300 to 500,000 such as from 500 to 100,000 g/mol.

The gelling agent may be chosen from olefin copolymers of controlled crystallization, as described in application EP-A-1 034 776 from the inventor, such as, for example, the ethylene/octene copolymer sold under the reference Engage 8400 by Dupont de Nemours.

This olefin copolymer or copolymers may be used for example at concentrations ranging from 0.5 to 20%, for example, from 1 to 10% of the total weight of the first composition.

In another non-limiting embodiment a polycaprolactone is used as a gelling agent.

The polycaprolactone may be chosen from, for example, ε-caprolactone homopolymers. Homopolymerization may be initiated with a diol, for example, a diol comprising 2 to 10 carbon atoms, such as diethylene glycol, 1,4-butanediol and neopentyl glycol.

It is possible, for example, to use polycaprolactones with a molecular weight ranging from 300 to 2,000 g/mol, such as those sold under the name Capa® 2125 by Solvay.

The polycaprolactone may be present in the composition in an amount ranging from 0.1 to 30% by weight, relative to the total weight of the composition, for example, from 0.5 to 25% by weight, for further example from 1 to 20% by weight, such as from 3 to 15% by weight.

In another non-limiting embodiment the gelling agent present in the composition disclosed herein may be an amorphous polymer formed by polymerizing an olefin as described in application EP 1 002 528, the content of which is incorporated into the present application by reference. The olefin may, for example, be an elastomeric ethylenically unsaturated monomer.

As examples of olefins mention may be made of ethylenic hydrocarbon monomers, having, for example, one or two ethylenic unsaturations and comprising 2 to 5' carbon atoms, such as ethylene, propylene, butadiene and isoprene.

An amorphous polymer is a polymer which does not have a crystalline form.

The amorphous polymeric gelling agent may be chosen from, for example, a diblock, triblock, multiblock, radial and star copolymer and mixtures thereof, for example, a triblock, multiblock, radial and star copolymer, and mixtures thereof.

Polymeric gelling agents of this kind are described in application US-A-2002/005562 and in U.S. Pat. No. 5,221,534.

The polymeric gelling agent may be an amorphous block copolymer of styrene and an olefin.

The polymeric gelling agent may be, for example, hydrogenated in order to reduce the ethylenic unsaturations which remain after the polymerization of the monomers.

For example, the polymeric gelling agent is an optionally hydrogenated copolymer comprising styrene blocks and ethylene/$C_3$-$C_4$ alkylene blocks.

The polymeric gelling agent may be a triblock copolymer, for example, hydrogenated, chosen from styrene-ethylene/propylene-styrene copolymers, styrene-ethylene/butadiene-styrene copolymers, styrene-isoprene-styrene copolymers and styrene-butadiene-styrene copolymers. Triblock polymers are sold, for example, under the names Kraton® G1650E, Kraton® G1652, Kraton® D1101, Kraton® D1102 and Kraton® D1160 by Kraton.

The amorphous polymeric gelling agent may be present in an amount ranging from 0.05% to 5% by weight, relative to the total weight of the composition, for example, ranging from 0.1% to 3% by weight, such as ranging from 0.2% to 2% by weight.

The polymer particles dispersed in the organic phase and the polymeric gelling agent may be present in the composition in an amount such that the weight ratio of dispersed and surface-stabilized polymer particles to polymeric gelling agent ranges from 10 to 30, from 15 to 25, such as from 18 to 22.

In another non-limiting embodiment the gelling agent may, for example, be chosen from:

pyrogenic silica, optionally hydrophobically treated on its surface, with a particle size of less than 10 microns;

optionally modified clays, such as hectorites modified with a $C_{10}$ to $C_{22}$ fatty acid ammonium chloride, such as hectorite modified with distearyldimethylammonium chloride and mixtures thereof.

As organic-phase gelling agents mention may also be made of the following:

partly or totally crosslinked elastomeric organopolysiloxanes of three-dimensional structure, such as those sold under the name KSG6, KSG16 and KSG18 by Shin-Etsu, Trefil E-505C and Trefil E-506C by Dow Corning, Gransil SR-CYC, SR DMF10, SR-DC556, SR 5CYC gel, SR DMF 10 gel and SR DC 556 gel by Grant Industries, and SF 1204 and JK 113 by General Electric;

galactomannans comprising from one to six, for example, from two to four hydroxyl groups per monosaccharide unit, which are substituted by a saturated or unsaturated alkyl chain, such as guar gum alkylated with $C_1$ to $C_6$, for example, $C_1$ to $C_3$ alkyl chains, such as the ethylated guar having a degree of substitution of from 2 to 3, such as that sold by Aqualon under the name N-Hance-AG;

gums, for example, silicone gums, such as PDMS gums, having a viscosity of more than 100 000 cSt, and mixtures thereof.

Colloidal Dispersion

The composition according to the invention comprises, for example, particles which are solid at ambient temperature and are dispersed in the physiologically acceptable medium, and which are introduced into the composition in the form of a colloidal dispersion, also referred to as a "particle paste", as described in application WO 02/39961, the content of which is incorporated by reference into the present application.

A colloidal dispersion or "particle paste" for the purposes of the invention is a concentrated colloidal dispersion of coated or uncoated particles in a continuous medium, this dispersion being stabilized using a dispersant or, where appropriate, without a dispersant. These particles may be chosen from pigments, nacres, solid fillers and mixtures thereof. These particles may be of any form, such as spherical or elongated such as fibres. They are insoluble in the medium.

In one embodiment, the purpose of the dispersant is to protect the dispersed particles against agglomeration or flocculation. The concentration of dispersant generally used to stabilize a colloidal dispersion ranges from 0.3 to 5 mg/m$^2$, for example, from 0.5 to 4 mg/m$^2$ of particle surface area. This dispersant may be chosen from a surfactant, an oligomer, a polymer or a mixture of two or more of these, and carries one or more functionalities which have a high affinity for the surface of the particles to be dispersed. For example, they are able to attach physically or chemically to the surface of the pigments. These dispersants additionally exhibit at least one functional group which is compatible with or soluble in the continuous medium. Use is made, for example, of esters of 12-hydroxystearic acid, such as of a $C_8$ to $C_{20}$ fatty acid and at least one polyol, such as glycerol or diglycerol, examples being poly(12-hydroxystearic) stearate with a molecular weight of approximately 750 g/mol, such as that sold under the name Solsperse 21 000 by Avecia, polyglyceryl-2 dipolyhydroxystearate (CTFA name), sold under the reference Dehymuls PGPH by Henkel, and also polyhydroxystearic acid, such as that sold under the reference Arlacel P100 by Uniqema, and mixtures thereof.

As other dispersants which can be used in the composition of the disclosure mention may be made of quaternary ammonium derivatives of polycondensed fatty acids, such as Solsperse 17 000 sold by Avecia and the polydimethylsiloxane/ oxypropylene mixtures such as those sold by Dow Corning under the references DC2-5185 and DC2-5225 C.

Polydihydroxystearic acid and the esters of 12-hydroxystearic acid are, for example, intended for a hydrocarbon-based or fluorine-based medium, while the dimethylsiloxane oxyethylene/oxypropylene mixtures are intended, for example, for a silicone-based medium.

The colloidal dispersion is a suspension of particles generally of micron size (<10 μm) in a continuous medium. The volume fraction of particles in a concentrated dispersion ranges from 20% to 40%, for example, from 30% to 40%, corresponding to a weight fraction which can range up to 70% depending on the density of the particles.

The particles dispersed in the medium may comprise particles chosen from mineral particles and organic particles and mixtures thereof as described below.

The continuous medium of the paste may be any medium and may comprise any solvent or liquid fatty substance and mixtures thereof. Advantageously the liquid medium of the particle paste is one of the liquid fatty substances or oils which it is desired to use in the composition, hence forming part of the liquid fatty phase.

The "particle paste" or colloidal dispersion may be a "pigment paste" comprising a colloidal dispersion of coloured, coated or uncoated, particles. These coloured particles are pigments, nacres or a mixture of pigments and/or nacres.

The colloidal dispersion may range in an amount from 0.5 to 60% by weight of the composition, for example, from 2 to 40%, such as from 2 to 30%.

The pigments may be white or coloured pigments, mineral and/or organic pigments, interference pigments or non-interference pigments. Among mineral pigments mention may be made of titanium dioxide, optionally with surface treatment, zirconium oxide or cerium oxide, and zinc oxide, iron oxide (black, yellow or red) or chromium oxide, manganese violet, ultramarine blue, chromium hydrate and ferric blue. Among organic pigments mention may be made of carbon black, organic lake pigments of barium, strontium, calcium or aluminium, including those certified by the U.S. Food and Drug Administration (FDA) (examples D&C or FD&C) and those exempt from FDA certification, such as lakes based on cochineal carmine. The pigments may range in amount from 0.1 to 50% in terms of active substance, for example, from 0.5 to 35%, such as from 2 to 25%, of the total weight of the composition.

The nacreous pigments may be chosen from white nacreous pigments such as titanium-covered mica and bismuth oxychloride; coloured nacreous pigments such as titanium mica with iron oxides, titanium mica with, for example, ferric blue or chromium oxide, titanium mica with an organic pigment of the aforementioned type; and also nacreous pigments based on bismuth oxychloride. They may range from 0 to 25% (in terms of active substance) of the total weight of the composition, for example, from 0.1 to 15% (if they are present). Use may therefore be made of pigments having goniochromatic properties and metal effect pigments, such as those described in the application filed under number FR 0 209 246, the content of which is hereby incorporated into the present application.

The fillers may be chosen from mineral, organic, lamellar, and spherical fillers. Mention may be made of talc, mica, silica, kaolin, Nylon® powders (Orgasol® from Atochem), poly-β-alanine powders and polyethylene powders, powders of polymers of tetrafluoroethylene (Teflon®), lauroyllysine, starch, boron nitride, hollow microspheres such as Expancel® (Nobel Industries), Polytrap® (Dow Corning) and silicone resin microbeads (Tospearls® from Toshiba, for example), precipitated calcium carbonate, magnesium carbonate and bicarbonate, hydroxyapatite, hollow silica microspheres (Silica Beads® from Maprecos), glass or ceramic microcapsules, metal soaps derived from organic carboxylic acids comprising from 8 to 22 carbon atoms, such as from 12 to 18 carbon atoms, for example zinc stearate, magnesium stearate or lithium stearate, zinc laurate and magnesium myristate.

Wax

Depending on the type of application envisaged, the composition according to the disclosure may further comprise at least one wax.

A wax for the purposes of the present disclosure is a lipophilic fatty compound which is solid at ambient temperature (25° C.) and exhibits a reversible solid/liquid state change, the compound having a melting temperature of greater than 40° C. and possibly up to 200° C. and having an anisotropic crystalline organization in the solid state. The size of the crystals is such that they diffract and/or scatter light, thereby endowing the composition with a turbid, more or less opaque appearance. By bringing the wax to its melting temperature it can be made miscible with the oils and made to form a microscopically homogeneous mixture; however, by bringing the temperature of the mixture back to ambient temperature, the wax is recrystallized in the oils of the mixture. It is this recrystallization in the mixture which is responsible for the decrease in the gloss of the mixture.

Linear hydrocarbon waxes may be used in the context of the present disclosure. Their melting point is advantageously greater than 35° C., for example greater than 55° C., such as greater than 80° C.

The linear hydrocarbon waxes may be chosen from substituted linear alkanes, unsubstituted linear alkanes, unsubstituted linear alkenes, substituted linear alkenes, an unsubstituted compound being comprised solely of carbon and hydrogen, and wherein the substituents mentioned above do not contain any carbon atoms.

Linear hydrocarbon waxes include polymers and copolymers of ethylene with a molecular weight ranging from 400 to 800, for example Polywax 500 or Polywax 400 sold by New Phase Technologies.

Linear hydrocarbon waxes include linear paraffin waxes, such as the paraffins S&P 206, S&P 173 and S&P 434 from Strahl & Pitsch.

Linear hydrocarbon waxes include long-chain linear alcohols, such as the products comprising a mixture of polyethylene and alcohols comprising from 20 to 50 carbon atoms, for example, Performacol 425 or Performacol 550 (mixture in 20/80 proportions) sold by New Phase Technologies.

The waxes may be present in an amount ranging from 2 to 30% by weight in the composition, for example, from 5 to 20%, such as from 5 to 15%, so as not excessively to diminish the gloss of the composition and of the film deposited on the lips and/or skin.

Additives and Pharmaceuticals

The composition of the disclosure may further comprise at least one cosmetic or dermatological active such as those conventionally employed.

As cosmetic, dermatological, hygienic or pharmaceutical actives which can be used in the composition disclosed herein mention may be made of moisturizers, vitamins, essential fatty acids, sphingolipids and sunscreens. These actives are used in an amount which is customary for the person skilled in the art, and, for example, at concentrations from 0 to 20%, such as from 0.001 to 15% of the total weight of the composition.

The composition may further comprise any other additive commonly used in such compositions, such as water, antioxidants, perfumes, preservatives and essential oils.

The person skilled in the art will of course take care to select this or these optional complementary compounds, and/ or their amount, such that the advantageous properties of the composition according to the invention are not, or not substantially, adversely affected by the intended addition.

In one non-limiting embodiment of the disclosure the compositions according to the invention may be prepared in customary manner by the person skilled in the art. They may be present in the form of a cast product, and for example in the form of a stick or crayon, or in the form of a dish, which can be used by direct contact or with a sponge. For example, they find application as a cast foundation, cast blusher or cast eyeshadow, lipstick, a care base or care balm for the lips or a concealer product. They may also be present in the form of a soft paste or else a gel, a more or less fluid cream, or a liquid, which are applied by means of a tube or with the finger. They may therefore be composed of foundations, or lipsticks, sun products or skin colouring products.

In one embodiment, the composition of the invention is anhydrous and in that case comprises less than 5% of water relative to the total weight of the composition.

These compositions for topical application may, for example, comprise a cosmetic, dermatological, hygienic or pharmaceutical composition for the protection, treatment or care of the face, neck, hands or body (for example care cream, sun oil, body gel), a makeup composition (for example a makeup gel, cream or stick) or an artificial tanning composition or skin protection composition.

The composition disclosed herein may be in the form of a dermatological or care composition for the skin and/or epidermal derivatives or in the form of a sun protection composition or a body hygiene composition, for example, in the form of a deodorant. In that case it is present, for example, in an uncoloured form. It may therefore be used as a care base for the skin, epidermal derivatives or lips (lip balms, protecting the lips from the cold and/or sun and/or wind, care cream for the skin, nails or hair).

The compositions disclosed herein may be lipsticks in the form of a stick or in fluid form.

In one embodiment, the composition disclosed herein must of course be cosmetically or dermatologically acceptable; that is, it must comprise a non-toxic, physiologically acceptable medium which can be applied to the skin, epidermal derivatives or lips of the face of human beings. A cosmetically acceptable composition for the purposes of the disclosure is a composition whose appearance, odour and feel are pleasant.

Two-Coat Makeup Product

The present disclosure likewise provides a cosmetic makeup product comprising first and second compositions, the first composition being composed of the composition described above, and the second composition comprising a second physiologically acceptable medium.

A makeup product is a product containing a colorant which allows a colour to be deposited on the keratin material (skin, lips or epidermal derivatives) of a human being by the application to the keratin material of products such as lipsticks, rouges, eyeliners, foundations or self-tanning products or semipermanent makeup products (tattoos).

When the makeup product is intended for making up the lips the first composition may be in the form of a stick or in a fluid form and the second composition may also be in the form of a stick or in a fluid form. A lip makeup product according to the disclosure comprises, for example, a first composition in the form of a stick, and a second composition in the form of a stick or in a fluid form packaged in a tube. The product disclosed herein may comprise two (or more) physiologically acceptable compositions packaged separately or together in a single container or in two (or more) separate or discrete containers.

In one non-limiting embodiment these compositions are packaged separately and, advantageously, in a single container having two ends.

The present disclosure therefore provides, for example, a cosmetic makeup product in the form of a foundation, blusher or eyeshadow, a lipstick, a product having care properties, for example, an eyeliner, a concealer product, or a body makeup product (of the tattoo type). The cosmetic makeup product is, for example, a lipstick.

The disclosure further provides a makeup kit comprising a cosmetic makeup product as defined above, in which the various compositions are packaged separately and are accompanied by appropriate means of application. These means may be fine brushes, coarse brushes, pens, pencils, felts, quills, sponges, tubes and/or foams. The composition can also be applied using the finger.

In one embodiment, the first composition of the product disclosed herein can be applied to the keratin material to form a basecoat, over which the second composition is deposited to give a topcoat or finish coat. Under the basecoat it is possible to apply an undercoat, whose composition is the same as or different from that of the second coat.

It is also possible to apply to the first topcoat a second topcoat identical to or different from the first in composition. The resulting makeup is preferably a makeup comprising a basecoat and a topcoat.

In some embodiments, the first composition is a foundation, face powder, lipstick, lipgloss, eyeliner or body makeup product and the second composition is a care product or a product intended for preserving or enhancing the cosmetic properties of the first composition, in particular its gloss and comfort.

The disclosure also relates to a method of making up the skin and/or lips and/or epidermal derivatives, which comprises applying to the skin and/or lips and/or epidermal derivatives a cosmetic makeup product as defined above.

The disclosure further provides a method of making up the skin and/or lips and/or epidermal derivatives of a human being, which comprises applying to the skin, lips and/or epidermal derivatives a first coat of a first composition comprising, in a physiologically acceptable medium, polymer particles dispersed in a liquid organic phase and a colorant and then applying, over all or part of the first coat, a second coat of a second composition comprising a physiologically acceptable medium.

More specifically, the method according to the invention comprises applying to the skin, lips and/or epidermal derivatives of a human being a first coat of a first composition comprising, in a first physiologically acceptable medium, polymer particles dispersed in a liquid organic phase and a colorant, in leaving the first coat to dry, and then applying, over all or part of the first coat, a second coat of a second composition comprising a second physiologically acceptable medium.

This two-coat makeup may be adapted to all makeup products for the skin both of the face and of the body, the mucosae, such as the lips, the inside of the lower eyelids, and the epidermal derivatives, such as nails, eyelashes, hair, eyebrows or even body hairs. The second coat can form designs and can be applied with a pen, pencil or any other instrument (sponge, finger, fine brush, coarse brush, quill, etc.). This makeup may also be applied to makeup accessories, such as false nails, false eyelashes, wigs or else discs or patches adhering to the skin or lips (of the beauty-spot type).

The disclosure additionally provides a made-up substrate comprising a first coat of a first composition comprising, in a first physiologically acceptable medium, polymer particles dispersed in a liquid phase, and a second coat of a second composition which is deposited over all or part of the first coat and comprises a second physiologically acceptable medium.

Second Composition

In one aspect of the disclosure the second composition according to the invention comprises at least one apolar or relatively apolar compound, which may be chosen from oils, gums and waxes. The second composition comprises, for example, more than 70%, for further example, more than 80% by weight, such as 100% by weight of apolar or relatively apolar compounds. These apolar or relatively apolar compounds are, for example, silicone compounds, colorants or gelling agents.

The second composition may be, for example, one of the compositions described in application U.S. 60/375,814, the content of which is hereby incorporated into the present application.

In one non-limiting embodiment of the disclosure the physiologically acceptable medium of the second composition comprises a liquid phase which is non-volatile at ambient temperature and atmospheric pressure.

Non-Volatile Liquid Phase of the Second Composition

The second composition may comprise from 15 to 90% by weight of at least one non-volatile liquid phase.

A "non-volatile liquid phase" is any medium apt to remain on the skin or lips for a number of hours. A non-volatile liquid phase has, for example, a non-zero vapour pressure at ambient temperature and atmospheric pressure, of less than 0.02 mm Hg (2.66 Pa), for example, less than $10^{-3}$ mm Hg (0.13 Pa).

The non-volatile liquid phase of the second composition is, for example, apolar or relatively apolar and, for example, comprises at least one of a liquid hydrocarbon oil, silicone oil and fluoro oil.

The non-volatile oils may be chosen from polydimethylsiloxanes; alkyldimethicones; polyphenylmethylsiloxanes such as phenyldimethicones and phenyltrimethicones; and silicones modified with aliphatic and/or aromatic groups, optionally fluorinated, or with functional groups such as hydroxyl, thiol and amine groups.

One non-volatile oil is an oil selected from the silicones of formula (I):

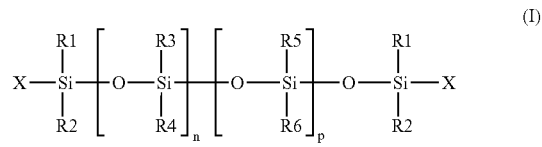

wherein:

$R_1$, $R_2$, $R_5$ and $R_6$, which may be identical or different, are chosen from alkyl radicals comprising from 1 to 6 carbon atoms, $R_3$ and $R_4$ are, which may be identical or different, are chosen from alkyl radicals comprising from 1 to 6 carbon atoms and aryl radicals, X is an alkyl radical comprising from 1 to 6 carbon atoms, a hydroxyl radical or a vinyl radical, and n and p are selected so as to endow the oil with a weight-average molecular mass of less than 200 000 g/mol, for example, less than 150 000 g/mol, such as less than 100 000 g/mol.

The non-volatile silicone oil of formula (I) selected is, for example, a polydimethylsiloxane with a viscosity ranging from 0.5 to 60 000 cSt, for example, from 0.5 to 10,000 cSt, for further example, from 0.5 to 1,000 cSt, such as DC 200, with a viscosity of 350 cSt, which is sold by Dow Corning.

In one non-limiting embodiment the non-volatile silicone oil of formula (I) is a polydimethylsiloxane with a viscosity ranging from 0.5 to 500 cSt, such as from 1 to 10 cSt.

The non-volatile liquid phase of the second composition may comprise, for example, at least one fluoro oil of formula (II):

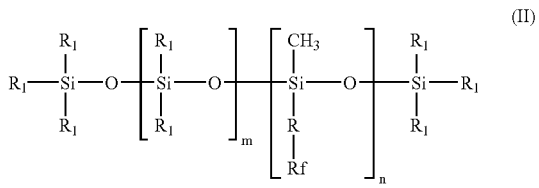

wherein:

R is chosen from linear and branched alkylenyl groups comprising from 1 to 6 carbon atoms, such as a divalent methylenyl, ethylenyl, propylenyl or butylenyl group, Rf is a fluoroalkyl radical, for example, a perfluoroalkyl radical, comprising from 1 to 9 carbon atoms, such as from 1 to 4 carbon atoms, $R_1$ is, independently at each occurrence, a $C_1$-$C_{20}$ alkyl radical, for example, a $C_1$-$C_4$ alkyl radical, a hydroxyl, or phenyl radical, m ranges from 0 to 150, such as from 20 to 100, and n is from 1 to 300, such as from 1 to 100.

Oils of formula (II) may be used such that $R_1$ is a methyl, R is an ethyl and Rf is $CF_3$. As fluorosilicone compounds of formula (II) mention may be made, for example, of those sold by Shin Etsu under the names X22-819, X22-820, X22-821 and X22-822 or else FL-100.

Among the fluoro oils mention may also be made of fluorinated polyethers chosen from the compounds of formula (III):

wherein:

$R_3$ to $R_6$, which may be identical or different, are monovalent radicals chosen from —F, —$(CF_2)_n$—$CF_3$ and —O—$(CF_2)_n$—$CF_3$, $R_7$ is a monovalent radical chosen from —F and —$(CF_2)_n$—$CF_3$, n ranges from 0 to 4 inclusive, p ranges from 0 to 600, q ranges from 0 to 860, r ranges from 0 to 1,500, p, q and r being integers selected such that the weight-average molecular mass of the compound is from 500 to 100 000, such as from 500 to 10,000.

The fluoro oils may also be chosen from fluorinated alkanes, for example, C2-C50 fluorinated alkanes, for further example, C5-C30, fluoroalkanes and perfluoroalkanes, such as perfluorodecalin, perfluoroadamantane and bromoperfluorooctyl and mixtures thereof.

The second composition may comprise a high molecular weight silicone polymer.

When the second composition disclosed herein is liquid it may comprise 20 to 50% by weight of a high molecular weight silicone polymer.

When the second composition disclosed herein is solid it may comprise from 2 to 40% by weight of a high molecular weight silicone polymer.

This polymer may be liquid or solid at ambient temperature and its weight-average molecular mass is greater than or equal to 200,000 g/mol, for example, from 200,000 to 2,500,000, such as from 200 000 to 2,000,000 g/mol.

The viscosity of this silicone polymer may be between 10,000 and 5,000,000 cSt, for example, from 100,000 to 1,000,000 cSt, such as from 300,000 to 700,000 cSt, measured in accordance with standard ASTM D-445.

The high molecular weight silicone polymer may be an ungrafted polymer, i.e. a polymer obtained by polymerizing at least one monomer without subsequent reaction of the side chains with another chemical compound. The silicone polymer may be chosen from, for example, dimethiconols, fluorosilicones, dimethicones and mixtures thereof. The polymer may be a homopolymer.

Use may be made in particular of a high molecular weight silicone polymer corresponding to the formula (IV):

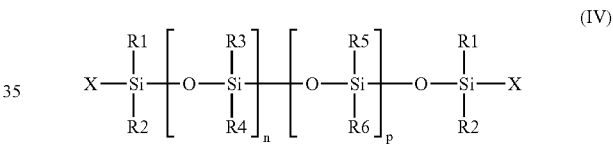

wherein:

$R_1$, $R_2$, $R_5$ and $R_6$, which may be identical or different, are chosen from alkyl radicals comprising from 1 to 6 carbon atoms optionally substituted by at least one fluorine atom, $R_3$ and $R_4$, which may be identical or different, are chosen from alkyl radicals comprising from 1 to 6 carbon atoms and aryl radicals, X is an alkyl radical comprising from 1 to 6 carbon atoms, a hydroxyl radical, a vinyl or allyl radical or an alkoxy radical comprising from 1 to 6 carbon atoms, and n and p are selected such that the silicone compound has a weight-average molecular mass of greater than or equal to 200,000 g/mol.

p may be, for example, 0.

The polymers of formula (IV) where $R_1$ to $R_6$ represent a methyl group and the substituent X represents a hydroxyl group are dimethiconols. Examples are the polymers of formula (III) where p 0 and n ranges from 2,000 and 40,000, for example, from 3,000 to 30,000.

The polymers have, for example, a molecular mass ranging from 1,500,000 to 2,000,000 g/mol.

In one non-limiting embodiment the high molecular weight silicone polymer is the dimethiconol sold by Dow Corning in a polydimethylsiloxane (5 cSt) under the reference D2-9085, the viscosity of the mixture being 1,550 cSt, or the dimethiconal sold by Dow Corning in octamethylcyclotetrasiloxane under the reference DC 1503. Likewise dimethiconol (with a molecular weight of 1 770 000 g/mol)

sold by Dow Corning under the reference Q2-1403 or Q2-1401, may be used, the viscosity of the mixture being 4,000 cSt.

As high molecular weight silicone polymers of formula (IV) which can be used according to the disclosure mention may be made of those for which:

the substituents $R_1$ to $R_6$ and X are a methyl group, such as that sold under the name SE30 by General Electric and that sold under the name AK 500000 by Wacker, the substituents $R_1$ to $R_6$ and X are a methyl group and p and n are such that the molecular weight is 250,000 g/mol, such as that sold under the name Silbione 70047 V by Rhodia, the substituents $R_1$ to $R_6$ are a methyl group and the substituent X is a hydroxyl group, such as that sold under the name Q2-1401 or Q2-1403 by Dow Corning, the substituents $R_1$, $R_2$, $R_5$, $R_6$ and X are a methyl group, the substituents $R_3$ and $R_4$ are an aryl group and n and p are such that the molecular weight of the polymer is 600,000 g/mol, such as that sold under the name 761 by Rhône-Poulenc.

The high molecular weight silicone polymer is preferably introduced into the composition in the form of a mixture with a liquid silicone, the viscosity of the liquid silicone being between 0.5 and 10,000 cSt, for example, from 0.5 to 500 cSt, such as from 1 to 10 cSt.

The silicone fluid may be chosen from polyalkylsiloxanes, polyarylsiloxanes, polyalkylarylsiloxanes and mixtures thereof. The liquid silicone may be a volatile silicone such as a cyclic polydimethylsiloxane comprising from 3 to 7 —$(CH_3)_2SiO$— units.

The liquid silicone may also be a non-volatile polydimethylsiloxane silicone, preferably with a viscosity of between 0.5 and 10,000 cSt, for example, of the order of 5 cSt, an example being the silicone sold as DC 200 by Dow Corning.

The proportion of the high molecular weight silicone polymer in the high molecular weight silicone polymer/liquid silicone mixture may be, for example, 10/90 and 20/80. The viscosity of the high molecular weight silicone polymer/liquid silicone mixture may be, for example, from 1,000 and 10,000 cSt.

The high molecular weight dimethicones according to the disclosure include the dimethicones described in U.S. Pat. No. 4,152,416. They are sold, for example, as SE30, SE33, SE54 and SE76.

The dimethicones according to the disclosure are, for example, compounds of formula (IV) such that $R_1$ to $R_6$ and X are methyls and p=0. The molecular weight of these polymers may range, for example, from 200,000 to 300,000, such as from 240,000 to 260 000 g/mol.

The dimethicones according to the invention include polydimethylsiloxanes, (polydimethylsiloxane)(methylvinylsiloxane) copolymers, poly(dimethylsiloxane)(diphenyl)(methylvinylsiloxane) copolymers, and mixtures thereof.

The high molecular weight fluorosilicones according to the disclosure may have, for example, a molecular weight ranging from 200,000 to 300,000, such as from 240,000 to 260,000 g/mol.

Wax in the Second Composition

The second composition may also comprises at least one wax, for example when it is in solid form.

The waxes may be present in an amount ranging from 2 to 30% by weight in the composition, for example, from 5 to 20%, such as from 5 to 15%, of the composition.

Linear hydrocarbon waxes may be used in the context of the present disclosure. Their melting point is advantageously greater than 35° C., for example greater than 55° C., such as greater than 80° C.

The linear hydrocarbon waxes may be chosen from substituted linear alkanes, unsubstituted linear alkanes, unsubstituted linear alkenes, substituted linear alkenes, an unsubstituted compound comprised solely of carbon and hydrogen, and wherein the substituents mentioned above do not contain any carbon atoms.

Linear hydrocarbon waxes include polymers and copolymers of ethylene with a molecular weight ranging from 400 to 800, for example Polywax 500 or Polywax 400, sold by New Phase Technologies.

Linear hydrocarbon waxes include linear paraffin waxes, such as paraffins S&P 206, S&P 173 and S&P 434 from Strahl & Pitsch.

Linear hydrocarbon waxes include long-chain linear alcohols, such as the products comprising a mixture of polyethylenes and alcohols comprising from 20 to 50 carbon atoms, in particular Performacol 425 or Performacol 550 (mixture in 20/80 proportions) sold by New Phase Technologies.

The second composition may comprise a silicone wax, such as a dimethicone comprising alkyl groups at the chain end. These alkyl groups, for example, may have more than 18 carbon atoms, for further example from 20 to 50, such as from 30 to 45 carbon atoms.

The silicone wax corresponds for example to the formula (V) or (VI)

$$R_3SiO {\begin{bmatrix} R \\ | \\ SiO \\ | \\ R \end{bmatrix}}_N SiR_3 \quad (V)$$

$$R-\underset{R}{\overset{R}{\underset{|}{Si}}}O {\begin{bmatrix} CH_3 \\ | \\ SiO \\ | \\ CH_3 \end{bmatrix}}_X {\begin{bmatrix} CH_3 \\ | \\ SiO \\ | \\ R \end{bmatrix}}_Y \underset{R}{\overset{R}{\underset{|}{Si}}}-R \quad (VI)$$

wherein R is an alkyl, X is greater than or equal to zero, and N and Y are greater than or equal to one.

R comprises from 1 to 50 carbon atoms, subject to the proviso that the compound is solid at ambient temperature.

Examples of silicone waxes include:

C20-C24 alkyl methicones, C24-C28 alkyl dimethicones, C20-C24 alkyl dimethicones and C24-C28 alkyl dimethicones, sold by Archimica Fine Chemicals as SilCare 41M40, SilCare 41M50, SilCare 41M70 and SilCare 41M80, stearyl dimethicones referenced SilCare 41M65, sold by Archimica, or referenced DC-2503, sold by Dow Corning, stearoxytrimethylsilanes sold as SilCare 1M71 or DC-580 the products Abil Wax 9810, 9800 or 2440 from Wacker-Chemie GmbH,

C30-45 alkyl methicones sold by Dow Corning as AMS-C30 Wax, and also C30-45 alkyl dimethicones sold as SF1642 or SF-1632 by General Electric.

Gelling Agent

The second composition may comprise a gelling agent as described herein.

Colorant

The second composition of the cosmetic makeup product according to the disclosure may comprise a colorant, which may be chosen from water-soluble and fat-soluble dyes, pigments, nacres and mixtures thereof.

Pigments are white or coloured, organic or mineral particles which are insoluble in the liquid organic phase and are intended for colouring and/or opacifying the first composition.

Nacres are iridescent particles, produced in particular by certain molluscs within their shell, or else synthesized, which are insoluble in the medium of the first composition.

Dyes are compounds, generally organic compounds, which are soluble in fatty substances, such as oils, or in an aqueous-alcoholic phase.

The fat-soluble dyes are, for example, Sudan Red, D&C Red No. 17, D&C Green No. 6, β-carotene, soya oil, Sudan Brown, D&C Yellow No. 11, D&C Violet No. 2, D&C Orange No. 5, quinoline yellow, annatto and bromo acids.

The water-soluble dyes are, for example, beetroot juice, methylene blue and caramel.

The pigments may be white or coloured pigments, mineral and/or organic pigments, interference pigments or non-interference pigments. Among mineral pigments mention may be made of titanium dioxide, optionally with surface treatment, zirconium oxide or cerium oxide, and zinc oxide, iron oxide (black, yellow, brown or red) or chromium oxide, manganese violet, ultramarine blue, chromium hydrate and ferric blue. Among organic pigments mention may be made of carbon black, organic lake pigments of barium, strontium, calcium or aluminium, including those certified by the U.S. Food and Drug Administration (FDA) (examples D&C or FD&C) and those exempt from FDA certification, such as lakes based on cochineal carmine.

The nacreous pigments may be chosen from white nacreous pigments such as titanium-covered mica and bismuth oxychloride, coloured nacreous pigments such as titanium mica with iron oxides, titanium mica with, for example, ferric blue or chromium oxide, titanium mica with an organic pigment of the aforementioned type, and also nacreous pigments based on bismuth oxychloride. Use may therefore be made of pigments having goniochromatic properties, for example, with liquid crystals or multilayered, and/or metal effect pigments, such as those described in the application filed under number FR 0 209 246, the content of which is hereby incorporated into the present application.

The second composition of the product according to the disclosure may also, but need not necessarily, comprise a colorant.

Generally speaking, the colorants range in amount from 0.001 to 600%, for example, from 0.01 to 50%, such as from 0.1 to 40% of the total weight of each first and second composition.

The colorant or filler may additionally be present in the form of a "particle paste".

Pharmaceuticals of the Makeup Product

Each composition of the two-coat makeup product according to the disclosure may be present in any pharmaceutical form which is normally used for topical application, for example, in the form of an oily or aqueous solution, an oily or aqueous gel, an oil-in-water or water-in-oil emulsion, a multiple emulsion, a dispersion of oil in water which is mediated by vesicles, the vesicles being situated at the oil/water interface, or a powder. Each composition may be fluid or solid.

In one embodiment, the first or the second composition, or both, have a continuous fatty phase and are, for example, in anhydrous form, and may comprise less than 5% of water, for example less than 1% of water, relative to the total weight of the first or second composition. For example, the overall two-coat makeup product may be in anhydrous form.

Each first and second composition may have the appearance of a lotion, cream, ointment, soft paste, salve, a cast or moulded solid, for example in stick form or dish form, or else a compacted solid.

Each composition may be, for example, in the form of a more or less rigid stick.

Each composition may be packaged separately in a single container, for example in a twin-compartment pen, the base composition being delivered by one end of the pen and the top composition being delivered by the other end of the pen, each end being closed, for example, tightly, by means of a cap.

The composition which is applied in a first coat is, for example in solid form, allowing more practical application, better temporal stability and temperature stability of the composition, and a precise line of the makeup, which is highly desirable in the case of a lipstick or an eyeliner.

The product according to the disclosure may be used for making up the skin and/or lips and/or epidermal derivatives, in accordance with the nature of the ingredients employed. For example, the product of the disclosure may be in the form of a solid foundation, a lipstick or lipstick paste, a concealer product, an eyeliner, a mascara, an eyeshadow, a body makeup product or else a skin-colouring product.

The product is, for example, a lipstick.

The first and/or the second composition may be in solid form.

The topcoat advantageously has properties of care, gloss and transparency.

The invention further provides a lip product, a foundation, a tattoo, a blusher or an eyeshadow which comprises a first and a second composition as described above.

The compositions of the disclosure may be obtained by heating the various constituents at the melting temperature of the highest waxes, then casting the melted mixture in a mould (dish or glove finger). They may also be obtained by extrusion as described in application EP-A-0 667 146.

The invention is illustrated in more detail in the following examples. The percentages are percentages by weight.

EXAMPLE 1

Polymer Dispersion

A dispersion was prepared of an uncrosslinked copolymer of methyl acrylate and acrylic acid in a 95/5 ratio in isododecane by the method of Example 1 of EP-A-749 746, replacing the heptane by isododecane. This gave a dispersion of poly (methyl acrylate/acrylic acid) particles surface-stabilized in isododecane by a block polystyrene/copoly(ethylene-propylene) diblock copolymer sold under the name Kraton G1701, having a solids content of 25% by weight.

EXAMPLE 2

Lipstick

| | |
|---|---|
| Polyethylene wax | 10.5% |
| (weight-average molecular mass: 500) | |
| Linear fatty alcohols | 2.5% |
| (Performacol 550 alcohol, sold by | |
| New Phase Technologies) | |
| Dispersion of Example 1 | 68% |
| Sucrose acetate isobutyrate | 5% |
| (Eastman SAIB sold by Eastman Chemical) | |
| Pigment paste | 13.5% |
| Perfume | 0.5% |

A heating vessel was charged with the polyethylene wax, the C30-C50 alcohols and the pigment paste, which were heated at 100° C. with magnetic stirring to give a homogeneous mixture. The composition of the pigment paste was 70% pigments, 1% poly(12-hydroxystearic) stearate and 29% hydrogenated polyisobutene. Subsequently the sucrose acetate isobutyrate and the dispersion of Example 1 were added, while maintaining the temperature and the stirring. The composition was cast into moulds at 40° C. and the moulds were cooled at −20° C. for thirty minutes. The sticks were then demoulded. The resulting sticks were homogeneous in colour and went on well. They resulted in a deposit on the lips which had staying power, did not migrate or transfer and was not sticky.

EXAMPLE 3

Lipstick as First Composition

| | |
|---|---|
| Polystyrene/poly(ethylene-propylene) Kraton G-1650E (sold by Kraton) | 0.5% |
| Dispersion of Example 1 | 65% |
| Polycaprolactone (Capa 2125, manufactured by Solvay) | 10% |
| Sucrose acetate isobutyrate (Eastman SAIB, sold by Eastman Chemical) | 10% |
| Pigment paste | 13.5% |
| Fragrance | qs |
| Preservative | qs |

The polycaprolactone was melted at 100° C. and then the pigment paste, whose composition is identical to that of Example 2, was added with stirring. Subsequently the other ingredients were added until a homogeneous mixture was obtained. The mixture was subsequently cooled to ambient temperature and packaged in pots.

EXAMPLE 4

Liquid Second Composition

| | |
|---|---|
| Polydimethylsiloxane sold as Silbione 70047 V by Rhodia (500 000 cSt - 250 000 g/mol) | 40% |
| Polydimethylsiloxane sold by Dow Corning as DC200 (5 cSt) | 60% |

The two ingredients were mixed at 70° C. using a Rayneri stirrer.

EXAMPLE 5

Solid Second Composition

| | % by weight |
|---|---|
| Silicone oil (PDMS) DC200 from Dow Corning (5 cSt) | 25 |
| Dimethicone (and) dimethiconol D2-9085 from Dow Corning (1550 cSt) | 61 |
| Trifluoropropyl dimethicone (100 cSt) X22-819 from Shin Etsu | 1 |
| C30-45 alkyl dimethicone (SF 1642 from GE Bayer Silicone) | 5 |
| Polyethylene wax (weight-average MW: 500) | 8 |

The silicone oil, dimethiconol and fluorinated dimethicone were mixed in hot form until a homogeneous mixture was formed. Thereafter the $C_{30}$-$C_{45}$ alkyl dimethicone was added to the first mixture, which was heated at 110° C. The polyethylene wax was subsequently added gradually until a homogeneous mixture was obtained. The mixture was cooled to 90-95° C. and then poured into moulds, which were cooled at −20° C. for thirty minutes. The sticks were subsequently demoulded.

What is claimed is:

1. A cosmetic composition comprising
   a) at least one liquid fatty phase and
   b) a dispersion of at least one polymer particle dispersed in the at least one liquid fatty phase, and
   c) at least one ester of at least one carboxylic acid and of at least one polyol, the at least one ester having a molecular mass of less than 5,000 g/mol, the at least one carboxylic acid comprising from 1 to 7 carbon atoms, and the at least one polyol comprising at least 4 hydroxyl groups.

2. The composition according to claim 1, wherein the at least one ester has a molecular mass of less than 2,000 g/mol.

3. The composition according to claim 2, wherein the at least one ester has a molecular mass of less than 1,000 g/mol.

4. The composition according to claim 3, wherein the at least one ester has a molecular mass of less than 900 g/mol.

5. The composition according to claim 1, wherein the at least one polyol is chosen from monosaccharides and polysaccharides comprising from one to 10 monosaccharide units.

6. The composition according to claim 5, wherein the at least one polyol is chosen from monosaccharides and polysaccharides comprising from one to 4 monosaccharide units.

7. The composition according to claim 6, wherein the at least one polyol is chosen from monosaccharides and polysaccharides comprising one or two monosaccharide units.

8. The composition according to claim 1, wherein the at least one polyol is chosen from monosaccharides and monosaccharide derivatives chosen from erythritol, xylitol, sorbitol and glucose.

9. The composition according to claim 1, wherein the at least one polyol is chosen from disaccharides.

10. The composition according to claim 9, wherein the disaccharide is sucrose.

11. The composition according to claim 1, wherein the at least one ester comprises no polar group chosen from ionic and non-ionic polar groups.

12. The composition according to claim 11, wherein the non-ionic polar groups are chosen from —COOH; —OH; ethylene oxide; propylene oxide; —PO$_4$; —NHR; and —NR$_1$R$_2$, wherein R$_1$ and R$_2$, which may be identical or different, optionally form a ring and are chosen from linear and branched C$_1$ to C$_{20}$ alkyl and alkoxy radicals.

13. The composition according to claim 1, wherein the at least one ester is an ester of at least two different monocarboxylic acids.

14. The composition according to claim 13, wherein the at least one ester is an ester of two monocarboxylic acids each comprising from 1 to 5 carbon atoms.

15. The composition according to claim 1, wherein at least one the carboxylic acid is chosen from linear and branched, unsubstituted acids.

16. The composition according to claim 14, wherein the at least one carboxylic acid is chosen from acetic, n-propanoic, isopropanoic, n-butanoic, isobutanoic, tert-butanoic, n-pentanoic and benzoic acids.

17. The composition according to claim 1, wherein the at least one ester is sucrose diacetate hexa(2-methylpropanoate).

18. The composition according to claim 1, wherein the at least one polymer particle is surface-stabilized in the at least one liquid fatty phase by at least one stabilizer.

19. The composition according to claim 1, wherein the at least one polymer particle has a mean size ranging from 5 to 800 nm.

20. The composition according to claim 1, wherein the at least one polymer particle is insoluble in water-soluble alcohols.

21. The composition according to claim 1, wherein the at least one polymer particle is chosen from polyurethanes, acrylic polyurethanes, polyureas, polyurea-polyurethanes, polyester-polyurethanes, polyether-polyurethanes, polyesters, polyester amides, fatty-chain polyesters, alkyds; acrylic and/or vinyl polymers or copolymers; acrylic-silicone copolymers; polyacrylamides; silicone polymers, fluoro polymers, and mixtures thereof.

22. The composition according to claim 1, wherein the at least one polymer particle is filmable.

23. The composition according to claim 1, wherein the at least one polymer particle ranges in amount, in terms of dry matter, from 5 to 40% of the total weight of the composition.

24. The composition according to claim 23, wherein the at least one polymer particle ranges in amount, in terms of dry matter, from 5 to 35% of the total weight of the composition.

25. The composition according to claim 24, wherein the at least one polymer particle ranges in amount, in terms of dry matter from 8 to 30% of the total weight of the composition.

26. The composition according to claim 18, wherein the at least one stabilizer is chosen from block polymers, graft polymers, and random polymers.

27. The composition according to claim 18, wherein the at least one stabilizer is chosen from graft block polymers and block polymers comprising at least one block resulting from the polymerization of diene and at least one block of a vinyl polymer.

28. The composition according to claim 27, wherein the at least one stabilizer is a diblock polymer.

29. The composition according to claim 1, wherein the composition comprises a colloidal dispersion of particles which are solid at ambient temperature and are chosen from pigments, nacres and mixtures thereof.

30. The composition according to claim 29, wherein the colloidal dispersion ranges from 0.5 to 60% by weight of the composition.

31. The composition according to claim 30, wherein the colloidal dispersion ranges from 2 to 40% by weight of the composition.

32. The composition according to claim 31, wherein the colloidal dispersion ranges from 2 to 30% by weight of the composition.

33. The composition according to claim 29, wherein the colloidal dispersion comprises a particle dispersant chosen from poly(12-hydroxystearic)stearate, poly(12-hydroxystearic)acid, diglyceryl 2-dipolyhydroxystearate and mixtures thereof.

34. The composition according to claim 29, wherein the colloidal dispersion comprises a fatty substance which is liquid at ambient temperature.

35. The composition according to claim 34, wherein the fatty substance which is liquid at ambient temperature is hydrogenated polyisobutene.

36. The composition according to claim 1, wherein the at least one liquid fatty phase comprises a non-volatile fatty phase and a volatile fatty phase.

37. The composition according to claim 36, wherein the volatile fatty phase comprises at least one oil chosen from $C_8$-$C_{16}$ isoalkanes.

38. The composition according to claim 37, wherein the volatile fatty phase comprises at least one oil chosen from isododecane and isohexadecane.

39. The composition according to claim 1, wherein the composition is substantially free of silicone oil.

40. The composition according to claim 1, wherein the composition is substantially free of fatty alcohol.

41. The composition according to claim 36, wherein the non-volatile fatty phase is apolar.

42. The composition according to claim 41, wherein the non-volatile fatty phase comprises at least one hydrocarbon oil.

43. The composition according to claim 42, where the hydrocarbon is hydrogenated polyisobutene.

44. The composition according to claim 1, wherein the composition comprises a gelling agent chosen from polymeric gelling agents and mineral gelling agents.

45. The composition according to the claim 44, wherein the gelling agent is a polymeric gelling agent chosen from amorphous block copolymers of styrene and olefin.

46. The composition according to claim 45, wherein the polymeric gelling agent is advantageously a triblock copolymer chosen from styrene-ethylene/propylene-styrene copolymers, styrene-ethylene/butadiene-styrene copolymers, styrene-isoprene-styrene copolymers and styrene-butadiene-styrene copolymers.

47. The composition according to claim 46, wherein the triblock copolymer is hydrogenated.

48. The composition according to claim 44, wherein the gelling agent is present in an amount ranging from 0.1 to 5% by weight, relative to the total weight of the composition.

49. The composition according to claim 48, wherein the gelling agent is present in an amount ranging from 0.2 to 3% by weight, relative to the total weight of the composition.

50. The composition according to claim 49, wherein the gelling agent is present in an amount ranging from 0.5 to 2% by weight, relative to the total weight of the composition.

51. The composition according to claim 44, wherein the gelling agent is a polymeric gelling agent chosen from polycaprolactones.

52. The composition according to claim 51, wherein the polycaprolactones are chosen from ε-caprolactone homopolymers with a molecular weight ranging from 300 to 2,000 g/mol.

53. The composition according claim 1, wherein the composition comprises at least one wax.

54. The composition according claim 1, wherein the at least one wax is chosen from ethylene polymers and copolymers, and linear alcohols comprising 20 to 50 carbon atoms.

55. The composition according to claim 1, wherein the composition is in a form chosen from a stick or bar, a smooth paste, and a liquid.

56. The composition according to claim 1, wherein the composition is in anhydrous form.

57. The composition according to claim 1, wherein the composition is in the form of a product for caring for and/or making up the skin and/or lips.

58. The composition according to claim 1, wherein the composition is in a form chosen from a foundation, a blusher or eyeshadow, a lipstick, a care base or care balm for the lips, a concealer product, an eyeliner and a mascara.

59. A method of cosmetic care or makeup of the lips or skin, comprising applying to the lips or skin a cosmetic composition comprising
   a) at least one liquid fatty phase and
   b) a dispersion of polymer particles dispersed in the said fatty phase, and c) at least one ester of at least one carboxylic acid and of at least one polyol; the ester having a molecular mass of less than 5,000 g/mol, the at least one carboxylic acid comprising 1 to 7 carbon atoms and the at least one polyol comprising at least 4 hydroxyl groups.

60. A method of limiting the transfer and/or enhancing the staying power and/or facilitating the application of a composition for making up or caring for the skin or lips, comprising applying to the skin or lips a composition,
wherein the composition comprises
a) at least one liquid fatty phase, and
b) a dispersion of at least one polymer particle dispersed in the at least one liquid fatty phase, and introducing into the liquid fatty phase at least one ester of at least one acid and of at least one polyol, the at least one ester having a molecular mass of less than 5,000 g/mol, the at least one acid comprising 1 to 7 carbon atoms, and the at least one polyol comprising at least 4 hydroxyl groups.

61. A method of making a composition for application to the skin, lips and epidermal integuments comprising adding to the composition
i) particles of at least one polymer dispersed in at least one liquid fatty phase and surface-stabilized by at least one stabilizer, and
ii) an ester of at least one acid and of at least one polyol, the at least one ester having a molecular mass of less than 5,000 g/mol, the at least one acid comprising from 1 to 7 carbon atoms, and the at least one polyol comprising at least 4 hydroxyl groups, wherein the composition enhances the non-transfer quality of the composition and/or enhances its staying power over time, and/or facilitates its application.

62. A cosmetic makeup product comprising
a first composition comprising
a) at least one liquid fatty phase and
b) a dispersion of at least one polymer particle dispersed in the at least one liquid fatty phase, and
c) at least one ester of at least one carboxylic acid and of at least one polyol, the at least one ester having a molecular mass of less than 5,000 g/mol, the at least one carboxylic acid comprising from 1 to 7 carbon atoms, and the at least 1 poloyl comprising at least 4 hydroxyl groups, and
a second composition comprising a physiologically acceptable medium.

* * * * *